US008748136B2

(12) United States Patent
Figge et al.

(10) Patent No.: US 8,748,136 B2
(45) Date of Patent: Jun. 10, 2014

(54) PRODUCING METHIONINE WITHOUT N-ACYL-METHIONINE

(75) Inventors: Rainer Figge, Riom (FR); Philippe Soucaille, Deyme (FR); Gwénaëlle Bestel-Corre, Saint Beauzire (FR)

(73) Assignee: Metabolic Explorer, Saint Beauzire (FR)

( * ) Notice: Subject to any disclaimer, the term of this patent is extended or adjusted under 35 U.S.C. 154(b) by 892 days.

(21) Appl. No.: 12/370,422

(22) Filed: Feb. 12, 2009

(65) Prior Publication Data

US 2010/0047879 A1    Feb. 25, 2010

Related U.S. Application Data

(63) Continuation-in-part of application No. PCT/EP2008/061005, filed on Aug. 22, 2008.

(51) Int. Cl.
*C12P 13/12* (2006.01)
*C07K 14/00* (2006.01)
*C07H 21/00* (2006.01)
*C12N 15/00* (2006.01)
*C12P 21/00* (2006.01)
*C12N 9/10* (2006.01)
*C12N 1/21* (2006.01)

(52) U.S. Cl.
USPC ........ 435/113; 435/440; 435/320.1; 435/193; 435/69.1; 435/252.33; 530/350; 536/23.2

(58) Field of Classification Search
USPC .................... 435/113, 440, 320.1, 69.1, 193; 530/350; 536/23.2
See application file for complete search history.

(56) References Cited

U.S. PATENT DOCUMENTS

| 2005/0026258 A1 | 2/2005 | Ptitsyn et al. |
| 2010/0047880 A1 | 2/2010 | Figge et al. |

FOREIGN PATENT DOCUMENTS

| EP | 1659174 | 5/2006 |
| WO | WO0170776 | 9/2001 |
| WO | WO03023044 | 3/2003 |
| WO | WO2005090589 | 9/2005 |
| WO | WO 2007/024756 | * 3/2007 |
| WO | WO2007077041 | 7/2007 |
| WO | WO2009043372 | 4/2009 |

OTHER PUBLICATIONS

Mountain et al., Mol Gen Genet 197:82-89, 1984.*
Branden et al., Introduction to Protein Structure, Garland Publishing Inc., New York, p. 247, 1991.*
Witkowski et al., Biochemistry 38:11643-11650, 1999.*
Seffernick et al., J. Bacteriol. 183(8):2405-2410, 2001.*
Zhou et al. (Cell Mol Life Sci 63(19-20):2260-2290, 2006.*
Kozak, M., Gene 234:187-208, 1999.*
Sousa et al., Microbiology 148(Pt5):1291-1303, 2002.*
Neidhardt et al., Journal of Bacteriology 119(3):736-747, 1974.*
Raymond et al., Archives of Biochemistry and Biophysics 372(2):300-308, 1999.*
Howarth et al., Biochimica et Biophysica Acta 1350:123-127, 1997.*
Davies, et al., I-Methionine Sulfoximine, but Not Phosphinothricin, Is a Substrate for an Acetyltransferase (Gene PA4866) from *Pseudomonas aeruginosa*: Structural and Functional Studies, Biochemistry, 2007, 46 (7), pp. 1829-1839, Publication Date (Web): Jan. 25, 2007.
Durfee, et al., The Complete Genome Sequence of *Escherichia coli* DH10B: Insights into the Biology of a Laboratory Workhorse, Journal of Bacteriology, Apr. 2008, p. 2597-2606, vol. 190, No. 7.
Database UniProt [Online], Mar. 1, 2001, "SubName: Full=Putative uncharacterized protein;" retrieved from EBI accession No. Uniprot:Q9HUU7, Database accession No. Q9HUU7.
Database EMBL [Online], Jun. 23, 2009, "Pseudomonas aeruginosa PAO1, complete genome" Database accession No. AE004091, abstract.
Database Uni Prot [Online], May 20, 2008, "SubName : Full=Predicted acyltransferase with acyl-CoA N-acyltransferase domain;" XP002542267 retrieved from EBI accession No. Uniprot:BIXDF9, Database accession No. BIXDF9.
Baker, David H, Comparative Species Utilization and Toxicity of Sulfur Amino Acids, The American Society for Nutrition J. Nutr. 136:1670S-1675S, Jun. 2006.
Hippe, et al., Effect of Methionine and N-Acetylmethionine Fortification on the Flavor of Soy Bread and Soy Milk, Journal of Food Science, vol. 43 Issue 3, pp. 793-796, Aug. 25, 2006.
Klein, David C., Arylalkylamine N-Acetyltransferase: "the Timezyme", Feb. 16, 2007, The Journal of Biological Chemistry, 282, 4233-4237.
Lacalle, et al., Molecular analysis of the pac gene encoding a puromycin N-acetyl transferase from Streptomyces alboniger, Gene. Jul. 15, 1989;79(2):375-80.
Tan, et al., Herbicidal inhibitors of amino acid biosynthesis and herbicide-tolerant crops, Amino Acids, vol. 30, No. 2, Mar. 2006, pp. 195-204.
Zahringer, et al., Nourseothricin (streptothricin) inactivated by a plasmid pIE636 encoded acetyl transferase of *Escherichia coli*: location of the acetyl group, FEMS Microbiol Lett. Jul. 1, 1993;110(3):331-4.
Anderson, E.H., Growth Requirements of Virus-Resistant Mutants of *Escherichia Coli* Strain "B", Proc Natl Acad Sci U S A. May 1946; 32(5): 120-128.
Carrier, et al., Library of Synthetic 5 Secondary Structures to Manipulate mRNA Stability in *Escherichia coli*, Biotechnology Progress, vol. 15 Issue 1, pp. 58-64, Sep. 4, 2008.
Choi, et al., Secretory and extracellular production of recombinant proteins using *Escherichia coli*, Applied Microbiology and Biotechnology, vol. 64, No. 5 / Jun. 2004, pp. 625-635.

(Continued)

*Primary Examiner* — Delia Ramirez
(74) *Attorney, Agent, or Firm* — Shweta Chandra; Carol L. Francis; Bozicevic, Field & Francis, LLP

(57) ABSTRACT

The present invention relates to a method for the production of methionine or its derivatives by culturing a microorganism in an appropriate culture medium comprising a source of carbon and a source of sulphur. The microorganism and/or the culture medium and/or the process parameters were modified in a way that the accumulation of the by-product N-acyl-methionine (NAM) is reduced. The isolation of methionine or its derivatives from the fermentation medium is also claimed.

17 Claims, No Drawings

(56) References Cited

OTHER PUBLICATIONS

Datsenko, et al., One-step inactivation of chromosomal genes in *Escherichia coli* K-12 using PCR products, Proc Natl Acad Sci U S A. Jun. 6, 2000;97(12):6640-5.

Driessen, et al., The mechanism of N-terminal acetylation of proteins, CRC Crit Rev Biochem. 1985;18(4):281-325.

Gentzen, et al., Aminoacylase from *Aspergillus oryzae*. Comparison with the pig kidney enzyme, Z Naturforsch C. Jul.-Aug. 1980;35(7-8):544-50.

Giardina, et al., The rat kidney acylase I, characterization and molecular cloning Differences with other acylases I, European Journal of Biochemistry, vol. 267 Issue 20, pp. 6249-6255, Dec. 25, 2001.

Jacob-Dubuisson, et al., Protein secretion through autotransporter and two-partner pathways, Biochimica et Biophysica Acta (BBA)—Molecular Cell Research, vol. 1694, Issues 1-3, Nov. 11, 2004, pp. 235-257.

Javid-Majd, et al., Mechanistic analysis of the argE-encoded N-acetylornithine deacetylase, Biochemistry. Feb. 15, 2000;39(6):1285-93.

Jose, et al., The Autodisplay Story, from Discovery to Biotechnical and Biomedical Applications, Microbiology and Molecular Biology Reviews, Dec. 2007, p. 600-619, vol. 71, No. 4, pp. 1092-2172.

Liebl, et al., Requirement of chelating compounds for the growth of *Corynebacterium glutamicum* in synthetic media, Applied Microbiology and Biotechnology, vol. 32, No. 2 / Dec. 1989, pp. 205-210.

Manting, et al., *Escherichia coli* translocase: the unravelling of a molecular machine, Molecular microbiology 2000;37 (2):226-38.

Marvil, et al., N-acetylglutamate synthase of *Escherichia coli*: purification, characterization, and molecular properties. charJ Biol Chem. May 25, 1977;252(10):3295-303.

Polevoda, et al., Nα-terminal Acetylation of Eukaryotic Proteins,The Journal of Biological Chemistry, 275, Nov. 24, 2000, 36479-36482.

Riedel, et al., Characterization of the phosphoenolpyruvate carboxykinase gene from *Corynebacterium glutamicum* and significance of the enzyme for growth and amino acid production, J Mol Microbiol Biotechnol. Oct. 2001;3 (4):573-83.

Schafer, et al., Automated Sampling Device for Monitoring Intracellular Metabolite Dynamics, Analytical Biochemistry, vol. 270, Issue 1, May 15, 1999, pp. 88-96.

Shokri, et al., Cell and process design for targeting of recombinant protein into the culture medium of *Escherichia coli*, Appl Microbiol Biotechnol. Feb. 2003;60(6):654-64. Epub Dec. 14, 2002.

Figge, Rainer M., Methionine Biosynthesis in *Escherichia coli* and *Corynebacterium glutamicum*, Microbiology Monographs, vol. May 2007, pp. 163-193.

* cited by examiner

PRODUCING METHIONINE WITHOUT N-ACYL-METHIONINE

FIELD OF THE INVENTION

The present invention relates to a method for the production of methionine or its derivatives by culturing a microorganism in an appropriate culture medium comprising a source of carbon and a source of sulphur. The microorganism and/or the culture medium and/or the process parameters were modified in a way that the accumulation of the by-product N-acyl-methionine (NAM) is reduced. The isolation of methionine or its derivatives from the fermentation medium is also claimed.

INTRODUCTION

Sulphur-containing compounds such as cysteine, homocysteine, methionine or S-adenosylmethionine are critical to cellular metabolism and are produced industrially to be used as food or feed additives and pharmaceuticals. In particular, methionine, an essential amino acid, which cannot be synthesized by animals, plays an important role in many body functions. Currently D,L-methionine is produced by chemical synthesis from acrolein, methyl mercaptan and hydrogen cyanide. Increasing prices for petrol-derived precursors acrolein and methyl mercaptan coupled to the increasing methionine demand render microbial production of methionine attractive.

The pathway for L-methionine synthesis is well known in many microorganisms (reviewed in Figge R M (2006), ed Wendisch V F, Microbiol Monogr (5) Amino acid biosynthesis p164-185). *E. coli* and *C. glutamicum* methionine producer strains have been described in patent applications WO2005/111202, WO2007/077041, WO2007/012078 and WO2007/135188.

Methionine produced by fermentation needs to be purified from the fermentation broth. Cost-efficient purification of methionine relies on producer strains and production processes that minimize the amount of by-products in the fermentation broth. "By-products" originate from methionine transforming and/or degrading pathways. In particular these products are S-adenosyl-methionine (SAM), thio-methyl-ribose and the N-acyl-methionines (NAM) such as N-acetyl-methionine and N-propionyl-methionine. As shown in patent application PCT/EP2007/060433, *E. coli* methionine producer strains produce N-acetyl-methionine. *E. coli* also produces N-propionyl-methionine.

The production of NAM is not desirable, since it reduces methionine yield and renders purification of methionine more difficult. NAM can be transformed to methionine and acetate by the addition of NAM acylases at the end of the fermentation run, but this drastically increases the cost of the product. Therefore, it is necessary to reduce or eliminate the accumulation of NAM during the fermentation run. This requires a good understanding of the reactions that are responsible for the accumulation of NAM.

N-terminal acetylation of methionine as a co-translational process is one of the most common protein modifications in eukaryotes. Nevertheless, it is unlikely that N-acetyl-methionine is produced by N-terminal acetylases (for review see Polevoda & Sherman 2000 JBC 275, 47, pp 36479-36482), since methionine seems to be acetylated as a free amino acid in methionine producing bacteria and methionine acetylation as a co-translational process is rare in prokaryotes (Driessen et al. 1985, CRC Crit. Rev. Biochem. 18, 281-325). N-acetyl-methionine is most likely obtained by acetylating free L-methionine. N-acetylating enzymes, which possibly could acetylate methionine, have been described. For example, ArgA encodes an N-acetyl-glutamate synthase in *E. coli* (Marvil & Leisinger 1977 JBC 252, 10 pp. 3295-3303).

Up to now, enzymes able to catalyze the biosynthetic production of N-acetyl-methionine, N-propionyl-methionine or other methionine derivatives with longer acyl chains were unknown. Identification of the major methionine-N-acyl transferase activities and their attenuation in methionine producing microorganisms is thus crucial for the reduction of NAM production.

NAM accumulation may also be reduced by deacetylating the accumulated NAM to obtain methionine. Deacetylation of N-acyl groups from amino acids has been demonstrated in bacteria. For example, ArgE encoded N-acetylornithine deacetylase has a broad substrate spectrum and deacetylates efficiently N-acetylmethionine (Javid-Majd & Blanchard 2000 Biochemistry 39, 1285-93). Thus, overexpression of argE or other amino acid deacetylases, such as rat kidney acylase I (Giardina et al 2000 Eur. J. Biochem. 267, 6249-55), amino acid acylase from *Aspergillus niger* or pig kidney (Gentzen et al. 1980 Z. Naturforsch 35 c, 544-50) may reduce the accumulation of NAM.

Since NAM is exported into the extracellular space, the export of NAM acylases into the periplasm or extracellular space can be an advantage. Several export systems are known in *E. coli* that permit the export into the periplasm, for example systems TAT and Sec (reviewed in Manting & Driessen 2000 Mol Microbiol 37, 226-38, Choi & Lee 2004 Appl. Microbiol. Biotechnol. 64, 625-635). Export via the TAT or Sec pathway requires the presence of specific signal peptides. If export into the extracellular space is favoured, the protein of interest may be fused to carrier proteins that are normally exported into the medium, such as OmpF or hemolysin (Choi & Lee 2004 Appl. Microbiol. Biotechnol. 64, 625-635). The protein can also be exported into the medium or displayed on the cell surface by fusing it to protein domains that are required for the export of autotransporter proteins, such as IgA1 from *N. gonorrhoeae* or AIDA-I from *E. coli*. Proteins may also be exported via the two-partner pathway or phage display (Jacob-Dubuisson et al. 2004 Biochim et Biophys Act 1694 235-257, Jose & Meyer 2007 Microbiol and Molecul Biol Rev 71, 600-19). Process design has also been shown to impact on the export of certain proteins (Shokri et al 2003 Appl Microbiol Biotechnol 60, 654-64).

SUMMARY

The applicants have solved the problem of reducing the accumulation of the by-product N-acyl-methionine (NAM) in methionine producer strains.

The inventors have identified the major methionine N-acyl-transferase activity (MNAT), which catalyzes the conversion of methionine to NAM, to be encoded by the gene yncA in *E. coli*.

A modified microorganism presenting an attenuation of the expression of the gene yncA, and therefore a reduced production of NAM, is here disclosed.

The inventors also showed that the overexpression of deacylating enzymes, such as *Aspergillus oryzae* amino acid acylase or pig kidney amino acid acylase, that convert NAM to methionine, lead to a decreased amount of NAM. Preferentially said deacylating enzymes are exported into the periplasm or into the extracellular space.

In another aspect, the culture conditions were adapted to obtain a reduction of the production and/or accumulation of NAM.

These three means to reduce the accumulation of NAM were applied individually or in combination, to reduce the accumulation of NAM.

Glucose is used as a model substrate and recombinant *E. coli* as model organism, but the invention is not limited to these features.

Accordingly, the object of the present invention is to provide a microorganism in which the expression of major MNAT (Methionine N-Acyl-Transferase) encoding genes have been attenuated, preferentially the corresponding genes deleted, and/or homologous or heterologous NAM deacylating enzymes have been overexpressed, to reduce the accumulation of NAM.

This microorganism with decreased NAM production and/or accumulation shows an improved methionine production/carbon source yield.

DETAILED DESCRIPTION OF THE INVENTION

The invention relates to a method for the production of methionine, its derivatives, or precursors in a fermentative process comprising the following steps:
 culturing a modified microorganism in an appropriate culture medium comprising a source of carbon, a source of sulphur and a source of nitrogen, and
 recovering methionine and/or its derivatives from the culture medium,
wherein compared to a non-modified microorganism or method, the microorganism or the method has been modified to reduce the accumulation of the by-product N-acyl methionine.

In a particular aspect of the invention, the N-acyl methionine whose accumulation is reduced is chosen among the following group: N-acetyl-methionine, N-propionyl-methionine, N-butyryl-methionine, and combinations thereof.

The accumulation of the by-product N-acyl methionine can be obtained by at least one of the following modifications:
 The attenuation of the expression of at least one methionine N-acyl transferase (i.e. transacylases) in the microorganism, and/or
 The expression (or enhancement of expression) of at least one methionine specific amino acylases in the microorganism; and/or
 The variation of culture conditions such as pH, oxygenation temperature, and/or addition of a NAM acylase into the culture medium,
and combinations thereof.

According to the invention the terms 'culture', "fermentation" or "fermentative process" are used interchangeably to denote the growth of bacteria on an appropriate growth medium containing a simple carbon source.

An "appropriate culture medium" is a medium appropriate for the culture and growth of the microorganism. Such media are well known in the art of microorganisms fermentation, depending upon the microorganism to be cultured.

The phrase "recovering methionine and/or its derivatives from the culture medium" designates the action of recovering methionine, and possibly SAM and NAM and all other derivatives that may be useful.

The term "microorganism" designates a bacterium, yeast or fungus. Preferentially, the microorganism is selected among Enterobacteriaceae, Bacillaceae, Streptomycetaceae and Coynebacteriaceae. More preferentially, the microorganism is a species of *Escherichia, Klebsiella, Pantoea, Salmonella* or *Corynebacterium*. Even more preferentially, the microorganism is either the species *Escherichia coli* or *Corynebacterium glutamicum*.

The term "modified microorganism" denotes a microorganism that has been genetically modified with the goal to reduce the accumulation of NAM in the fermentation broth. The man skilled in the art knows how to modulate the expression of specific genes. Usual modifications include transforming microorganisms with genetic elements, including deletions of genes, gene replacements, modification of promoters, and introduction of vectors for the expression of heterologous genes.

The inventors have shown that NAM is formed by acylation of methionine and have identified the gene yncA as the major NAM producing enzyme. yncA also known as *E. coli* gene b1448 has been mentioned in patent application WO2001070776. It is part of a group of genes induced by the regulator Mar, involved in multidrug resistance.

Amino acid acylase enzymes (EC 3.5.1.14), also called deacetylases, catalyze the hydrolytic cleavage of an acyl amino acid to produce the free amino acid and the carbonic acid corresponding to the acyl rest. More specifically N-acyl methionine acylases catalyze the reaction of NAM to methionine and the corresponding carboxy acid.

The term "N-acyl methionine" designates N-formyl-methionine, N-acetyl-methionine, N-propionyl-methionine, N-butyryl methionine and in general, any methionine derivative comprising a functional group derived from any carboxylic acid that lacks the hydroxyl function.

To measure the accumulation of N-acetyl-methionine, the amount of N-acetyl-methionine is determined in the fermentation broth using refractometric HPLC using N-acetyl-methionine (Sigma, Ref 01310) as a standard. N-propionyl-methionine is determined in the fermentation broth by GC-MS using N-acetyl-methionine as a standard.

The accumulation of NAM should be reduced at least by 20% preferentially 50%, more preferentially 80% and even more preferentially 95% of the amount accumulated in a process with the non-modified organism or in the non-modified process.

The term 'carbon source' according to the present invention denotes any source of carbon that can be used by those skilled in the art to support the normal growth of a microorganism, which can be hexoses (such as glucose, galactose or lactose), pentoses, monosaccharides, disaccharides (such as sucrose, cellobiose or maltose), oligosaccharides, molasses, starch or its derivatives, hemicelluloses, glycerol and combinations thereof. An especially preferred carbon source is glucose. Another preferred carbon source is sucrose.

In a particular embodiment of the invention, the carbon source is derived from renewable feed-stock. Renewable feed-stock is defined as raw material required for certain industrial processes that can be regenerated within a brief delay and in sufficient amount to permit its transformation into the desired product.

The term nitrogen source corresponds to either an ammonium salt or ammoniac gas. The nitrogen source is supplied in the form of ammonium or ammoniac.

The sulphur source used for the fermentative production of L-methionine, its precursors or compounds derived thereof, may be any of the following: sulfate, thiosulfate, hydrogen sulfide, dithionate, dithionite, sulfite, methylmercaptan, dimethyldisulfide or a combination thereof.

In a preferred embodiment of the invention, the sulphur source is sulfate and/or thiosulfate.

The fermentation is generally conducted in fermenters with an appropriate culture medium adapted to the microorganism being used, containing at least one simple carbon source, and if necessary co-substrates for the production of metabolites.

Those skilled in the art are able to define the culture conditions for the microorganisms according to the invention. In particular the bacteria are fermented at a temperature between 20° C. and 55° C., preferentially between 25° C. and 40° C., and more specifically about 30° C. for *C. glutamicum* and about 37° C. for *E. coli*.

As an example of known culture medium for *E. coli*, the culture medium can be of identical or similar composition to an M9 medium (Anderson, 1946, *Proc. Natl. Acad. Sci. USA* 32:120-128), an M63 medium (Miller, 1992; A Short Course in Bacterial Genetics: A Laboratory Manual and Handbook for *Escherichia coli* and Related Bacteria, Cold Spring Harbor Laboratory Press, Cold Spring Harbor, N.Y.) or a medium such as defined by Schaefer et al. (1999, *Anal. Biochem.* 270: 88-96).

As an example of known culture mefium for *C. glutamicum*, the culture medium can be of identical or similar composition to BMCG medium (Liebl et al., 1989, *Appl. Microbiol. Biotechnol.* 32: 205-210) or to a medium such as described by Riedel et al. (2001, *J. Mol. Microbiol. Biotechnol.* 3: 573-583).

In a specific embodiment of the invention, the production of N-acyl-methionine is reduced by attenuating at least one of the methionine transacylases. Methionine transacylases are also called methionine N-acyltransferase (MNAT). argA encodes an enzymes with putative methionine transacetylase activity. The inventors have purified MNAT activity from an *E. coli* strain with an argA deletion, sequenced the purified protein and shown that the purified protein, YncA has MNAT activity (patent application PCT/EP2008/060999). Attenuation of the expression of the gene yncA eliminates a large amount of the residual MNAT activity, leading to a dramatic reduction of NAM production, especially of compounds N-acetyl-methionine and N-propionyl-methionine. In a preferred embodiment of the invention, YncA is entirely deleted from the *E. coli* genome.

Other N-acyltransferases with a lower activity have been identified, that permit to obtain a reduced NAM production when attenuated; these enzymes are encoded by the following genes:, yjdJ, yfaP, yedL, yjhQ. Any of the described methionine N-acyl transferases may be attenuated individually or in combination with the others.

Terms "attenuating a gene" or 'attenuation of the expression of a gene' according to the invention denotes the partial or complete suppression of the expression of a gene, which is then said to be 'attenuated'. This suppression of expression can be either an inhibition of the expression of the gene, an insertion into or a deletion of all or part of the promoter region necessary for gene expression, a deletion or insertion in the coding region of the gene, or the exchange of the wildtype promoter by a weaker natural or synthetic promoter. Preferentially, the attenuation of a gene is essentially the complete deletion of that gene, which can be replaced by a selection marker gene that facilitates the identification, isolation and purification of the strains according to the invention. A gene is inactivated preferentially by the technique of homologous recombination (Datsenko, K. A. & Wanner, B. L. (2000) "One-step inactivation of chromosomal genes in *Escherichia coli* K-12 using PCR products". Proc. Natl. Acad. Sci. USA 97: 6640-6645).

In another specific embodiment of the invention, the accumulation of N-acyl-methionine may be reduced by expressing into the microorganism native or heterologous methionine specific amino acylase enzymes, such as:
  *Aspergillus* N-acylamino acid acylase
  Pig N-acylamino acid acylase

*E. coli* argE encoding acetylornithine deacetylase, acting also on N-acetylmethionine.

Increased expression of methionine specific amino acylases increases the conversion rate of NAM into methionine with the concomitant production of one molecule of the corresponding carboxy acid, such as acetate, priopionate or butyrate. Favouring the consumption of acetate by overexpressing the genes acs, pta-ackA or genes coding for the glyoxylate shunt is also part of the invention.

The terms "enhanced" or "overexpressed" in this context describe the increase in the intracellular activity of an enzymatic activity which is encoded by the corresponding DNA, for example by increasing the number of copies of the gene, using a stronger promoter or using an allele with increased activity and possibly combining these measures.

The terms "increased expression" "enhanced expression" or "overexpression" are used interchangeably in the text and have similar meaning.

To increase the expression of a gene it may be encoded chromosomally or extrachromosomally. Chromosomally there may be one or several copies on the genome that can be introduced by methods of recombination known to the expert in the field.

Extrachromosomally genes may be carried by different types of plasmids that differ with respect to their origin of replication and thus their copy number in the cell. They may be present as 1-5 copies, about 20 or up to 500 copies, corresponding to low copy number plasmids with tight replication (pSC101, RK2), low copy number plasmids (pACYC, pRSF1010) or high copy number plasmids (pSK bluescript II).

In a preferred embodiment of the invention, the gene may be expressed using promoters with different strength, which may be inducible. These promoters may be homologous or heterologous. The man skilled in the art knows which promoters are the most convenient, for example, promoters Ptrc, Ptac, Plac or the lambda promoter cI are widely used.

Expression of the enzymes may be boosted or reduced by elements stabilizing or destabilizing the corresponding messenger RNA (Carrier and Keasling (1998) Biotechnol. Prog. 15, 58-64) or the proteins (e.g. GST tags, Amersham Biosciences).

The present invention also relates to microorganisms that contain one or several alleles of the gene to be enhanced according to the invention.

All techniques for transforming the microorganisms, and regulatory elements used for enhancing the production of the protein of the invention are well known in the art and available in the literature, including applicant's own patent applications on modification of biosynthesis pathways in various microorganisms, including WO2008/052973, WO2008/052595, WO2008/040387, WO2007/144346, WO2007/141316, WO2007/077041, WO2007/017710, WO2006/082254, WO2006/082252, WO2005/111202, WO2005/073364, WO2005/047498, WO2004/076659, the content of which is incorporated herein by reference.

N-acyl-methionine acylase enzymes will be expressed in the intracellular space and may remain in the intracellular space or be exported into the periplasm or be exported into the extracellular space. The expert in the field will be able to identify means to target the protein to the periplasm. Export may also be based on fusing the N-acetyl-methionine acylases to proteins like OmpF, by phage display or by using protein export systems such as two-partner pathway or autotransport. In a preferred embodiment of the invention NAM acylase enzymes are exported into the periplasm or the extracellular compartment to avoid futile cycling between NAM and methionine.

In another embodiment of this invention, the inventors have adapted the parameters of the fermentation process, i.e. the culture conditions, to reduce the production of NAM. This is accomplished by changing the pH of the fermentation broth, modifying oxygenation or substrate feeding parameters. Another option is to add into the culture medium a NAM specific acylase.

In one embodiment, the change of the fermentation parameters does not include the starving of the microorganism for an inorganic substrate such as phosphate, potassium, magnesium.

These three means to modulate the accumulation of NAM can be used alone or combined with one or two of the other means.

Accordingly, the attenuation of the MNAT activity is obtained by attenuating the expression of the following genes: yncA and/or argA and/or, yjdJ, yfaP, yedL, yjhQ, these genes encoding enzymes with methionine-N-acyltransferases. This attenuation may be combined with the increased expression of the N-acyl-methionine deacylase enzymes, such as *Aspergillus* N-amino acid acylase, pig N-amino acid acylase or acetylornithine deacetylase encoded by the argE gene.

Similarly, the attenuation of at least one MNAT enzymes, as described above, may be combined with the adaptation of the process parameters, such as pH, oxygenation, temperature and/or by adding NAM acylase to the fermentation broth, permitting together a reduction of the accumulation of NAM.

Similarly, the expression of the NAM acylase enzymes may be combined with the adaptation of the process. Details of both means have been described above.

Finally, all three means may be combined: the attenuation of the MNAT activity, the increased expression of the NAM acylase enzymes and the adaptation of the process conditions.

In the description of the present invention, genes and proteins are identified using the denominations of the corresponding genes in *E. coli*. However, and unless specified otherwise, use of these denominations has a more general meaning according to the invention and covers all the corresponding genes and proteins in other organisms, more particularly microorganisms.

PFAM (protein families database of alignments and hidden Markov models) represents a large collection of protein sequence alignments. Each PFAM makes it possible to visualize multiple alignments, see protein domains, evaluate distribution among organisms, gain access to other databases, and visualize known protein structures.

COGs (clusters of orthologous groups of proteins are obtained by comparing protein sequences from fully sequenced genomes representing major phylogenic lines. Each COG is defined from at least three lines, which permits the identification of former conserved domains.

The means of identifying homologous sequences and their percentage homologies are well known to those skilled in the art, and include in particular the BLAST programs. The sequences obtained can then be exploited (e.g., aligned) using, for example, the programs CLUSTALW or MULTALIN, with the default parameters indicated on those websites.

Using the references given in GenBank for known genes, those skilled in the art are able to determine the equivalent genes in other organisms, bacterial strains, yeasts, fungi, mammals, plants, etc. This routine work is advantageously done using consensus sequences that can be determined by carrying out sequence alignments with genes derived from other microorganisms, and designing degenerate probes to clone the corresponding gene in another organism. These routine methods of molecular biology are well known to those skilled in the art, and are claimed, for example, in Sambrook et al. (1989 Molecular Cloning: a Laboratory Manual. 2$^{nd}$ ed. Cold Spring Harbor Lab., Cold Spring Harbor, N.Y.).

The present invention is also related to a microorganism such as described above. A microorganism with a reduced accumulation and/or production of N-acyl methionine is in particular useful for producing methionine with high yield. Preferentially, the microorganism according to the invention is already a high-producer of methionine before being used in the process according to the invention.

Efficient production of methionine requires the optimisation of the methionine specific pathway and several precursor-providing pathways. Methionine producing strains have been described in patent applications WO 2005/111202, WO2007/077041 and PCT/EP2007/060433 and are incorporated as reference into this application.

A methionine producing strain that overexpresses homoserine succinyltransferase alleles with reduced feedback sensitivity to its inhibitors SAM and methionine is described in patent application WO 2005/111202. This application describes also combination of these alleles with a deletion of the methionine repressor MetJ (GenBank 1790373), responsible for the down-regulation of the methionine regulon as was suggested in patent application JP 2000/157267. In addition, combinations of the two modifications with the overexpression of aspartokinase/homoserine dehydrogenase are described in patent application WO 2005/111202.

The overexpression of the genes cysE, metH and metF has been suggested in WO 2007/077041.

Production of methionine may be further increased by using an altered metB allele that uses preferentially or exclusively H$_2$S and thus produces homocysteine from O-succinylhomoserine as has been described in the patent application WO 2004/076659 that is incorporated herein by reference.

Further increase in methionine production may be obtained by deleting the genes pykA, pykF and/or purU as described in patent application PCT/EP2007/060433. This application also describes methionine-producing strains in which the operons cysPUWAM, cysJIH and gcvTHP and the genes serA, serB, serC, lpd and glyA are overexpressed.

In *E. coli*, other enzymes may be increased in their activity to increase the production of methionine (followed by accession numbers and function of the corresponding polypeptide):

The expression of the genes involved in sulphur assimilation may be increased:

| gene | accession number | function |
| --- | --- | --- |
| cysK | 1788754 | cysteine synthase |
| CysZ | g1788753 | ORF upstream of cysK |
| cysN | g1789108 | ATP sulfurylase |
| cysD | g1789109 | sulfate adenylyltransferase |
| cysC | g1789107 | adenylylsulfate kinase |
| cysZ | 1788753 | sulfate transport |
| sbp | 1790351 | Periplasmic sulfate-binding protein |

Anaplerotic reactions may be boosted by expressing

| ppc | 1790393 | phosphoenolpyruvate carboxylase |
| pps | 1787994 | phosphoenolpyruvate synthase |

Acetate consuming reactions may be boosted by over expressing acs 1790505 acetyl-CoA synthetase Furthermore expression of genes in pathways degrading methionine (see list below) or deviating from the methionine production pathway may be attenuated or the genes may be deleted.

Attenuation in this context describes the reduction of the intracellular activity of an enzyme by measures such as reducing its expression, reducing the stability of the enzyme, increasing its degradation and/or other solutions known to the expert in the field.

| Gene | Genbank entry | activity |
|------|---------------|----------|
| ackA | 1788633 | acetate kinase |
| pta | 1788635 | phosphotransacetylase |
| aceE | 1786304 | pyruvate deydrogenase E1 |
| aceF | 1786305 | pyruvate deydrogenase E2 |
| lpd | 1786307 | pyruvate deydrogenase E3 |
| sucC | 1786948 | succinyl-CoA synthetase, beta subunit |
| sucD | 1786949 | succinyl-CoA synthetase, alpha subunit |
| pck | 1789807 | phosphoenolpyruvate carboxykinase |
| poxB | 1787096 | pyruvate oxidase |
| ilvB | 1790104 | acetohydroxy acid synthase I, large subunit |
| ilvN | 1790103 | acetohydroxy acid synthase I, small subunit |
| ilvG | 1790202 1790203 | acetohydroxy acid synthase II, large subunit |
| ilvM | 1790204 | acetohydroxy acid synthase II, small subunit |
| ilvI | 1786265 | acetohydroxy acid synthase III, large subunit |
| ilvH | 1786266 | acetohydroxy acid synthase III, small subunit |
| aroF | 1788953 | DAHP synthetase |
| aroG | 1786969 | DAHP synthetase |
| aroH | 1787996 | DAHP synthetase |
| thrB | 1786184 | homoserine kinase |
| thrC | 1786185 | threonine synthase |
| sdaA | 1788116 | serine deaminase |
| sdaB | 1789161 | serine deaminase |
| speD | g1786311 | S-Adenosylmethionine decarboxylase |
| speC | g1789337 | Ornithine decarboxylase |
| astA | g1788043 | Arginine succinyltransferase |
| dapA | g1788823 | Dihydrodipicolinate synthase |

The invention also concerns the process for the production of L-methionine, its precursors or compounds derived thereof, comprising the fermentation of the methionine producing microorganism described above, the concentration of methionine, its precursors or derivatives and the isolation of the desired product(s) of the fermentation broth.

Those skilled in the art are able to define the culture conditions for the microorganisms according to the invention. In particular the bacteria are fermented at a temperature between 20° C. and 55° C., preferentially between 25° C. and 40° C., and more specifically about 30° C. for C. glutamicum and about 37° C. for E. coli.

The fermentation is generally conducted in fermenters with an inorganic culture medium of known defined composition adapted to the bacteria used, containing at least one simple carbon source, and if necessary a co-substrate necessary for the production of the metabolite.

In particular, the inorganic culture medium for E. coli can be of identical or similar composition to an M9 medium (Anderson, 1946, Proc. Natl. Acad. Sci. USA 32:120-128), an M63 medium (Miller, 1992; A Short Course in Bacterial Genetics: A Laboratory Manual and Handbook for Escherichia coli and Related Bacteria, Cold Spring Harbor Laboratory Press, Cold Spring Harbor, N.Y.) or a medium such as defined by Schaefer et al. (1999, Anal. Biochem. 270: 88-96).

Analogously, the inorganic culture medium for C. glutamicum can be of identical or similar composition to BMCG medium (Liebl et al., 1989, Appl. Microbiol. Biotechnol. 32: 205-210) or to a medium such as described by Riedel et al. (2001, J. Mol. Microbiol. Biotechnol. 3: 573-583). The media can be supplemented to compensate for auxotrophies introduced by mutations.

After fermentation, L-methionine, its precursors or compounds derived thereof, is/are recovered and purified if necessary. The methods for the recovery and purification of the produced compound such as methionine in the culture media are well known to those skilled in the art.

Optionally, from 0 to 100%, preferentially at least 90%, more preferentially 95%, even more preferentially at least 99% of the biomass may be eliminated during the purification of the fermentation product.

In a preferred embodiment of the invention, the method for the production of methionine comprises a step of isolation of the desired amino acids/constituents of the fermentation broth and/or the biomass optionally remaining in portions or in the total amount (0-100%) in the end product.

Means of reducing the amount of NAM may be combined with limitation or starvation for phosphate and/or potassium. The expert in the field will be able to determine the amounts of phosphate or potassium necessary for growth of the chosen organism.

"Subjecting an organism to a limitation of an inorganic substrate" defines a condition under which growth of the microorganisms is governed by the quantity of an inorganic chemical supplied that still permits weak growth. Examples for these substrates are phosphate, potassium, magnesium or a combination of these.

Starving a microorganism for an inorganic substrate defines the condition under which growth of the microorganism stops completely due to the absence of the inorganic substrate. Examples for these substrates are phosphate, potassium, magnesium or a combination of these.

The invention also relates to a microorganism such as described previously that is optimized for the fermentative production of methionine with a reduced accumulation of NAM, i.e. accumulating lower amounts of NAM compared to a non-modified microorganism, and the microorganism that comprises the genetic modifications described above.

EXAMPLES

Example 1

Construction of Strain MG1655 metA*11 ΔmetJ Ptrc-metH Ptrc36-ARNmst17-metF PtrcF-cysPU-WAM PtrcF-cysJIH ΔpykA ΔpykF Ptrc09-gcvTHP ΔpurU ΔyncA::Km (pME101-thrA*1-cysE-PgapA-metA*11) (pCC1BAC-serB-serA-serC)

To delete the putative acyltransferase yncA gene in a methionine producer strain, we used the Escherichia coli BW25113 ΔyncA::Km strain of the Keio mutant collection (Baba et al., 2006). The ΔyncA::Km deletion was transferred by P1 phage transduction (see below) from the BW25113 ΔyncA::Km strain to strain MG1655 metA*11 ΔmetJ Ptrc-metH Ptrc36-ARNmst17-metF PtrcF-cysPUWAM PtrcF-cysJIH Ptrc09-gcvTHP ΔpykA ΔpykF ΔpurU (described in PCT/EP2007/060433). Kanamycine resistant transformants were selected and the insertion of the resistance cassette was verified by PCR analysis with the oligonucleotides YncAF and YncAR defined below (reference sequence on the website ecogene.org/). The strain retained was designated MG1655 metA*11 ΔmetJ Ptrc-metH Ptrc36-ARNmst17-metF PtrcF-cysPUWAM PtrcF-cysJIH Ptrc09-gcvTHP ΔpykA ΔpykF ΔpurU ΔyncA::Km.

YncAF: GTTTGCCGATTTGCCCCACCG (homologous to the yncA region from 1517564 to 1517544) (SEQ ID NO 01)
 YncAR: CGCCCATCACGGTCGCAAGC (homologous to the yncA region from 1515827 to 1515846) (SEQ ID NO 02)

Then, the plasmids pME101-thrA*1-cysE-PgapA-metA*11 and pCC1BAC-serB-serA-serC were introduced into the strain MG1655 metA*11 ΔmetJ Ptrc-metH Ptrc36-ARNmst17-metF PtrcF-cysPUWAM PtrcF-cysJIH Ptrc09-gcvTHP ΔpykA ΔpykF ΔpurU ΔyncA::Km, giving rise to MG1655 metA*11 ΔmetJ Ptrc-metH Ptrc36-ARNmst17-metF PtrcF-cysPUWAM PtrcF-cysJIH Ptrc09-gcvTHP ΔpykA ΔpykF ΔpurU ΔyncA::Km (pME101-thrA* 1-cysE-PgapA-metA*11) (pCC1BAC-serB-serA-serC).

Preparation of Phase Lysate P1:
 Inoculation of 10 mL LB supplemented with kanamycin (50 μg/mL), glucose (0.2%) and CaCl$_2$ (5 mM) with 100 μL overnight culture of the strain BW25113 ΔyncA::Km
 Incubation for 30 min at 37° C. with shaking
 Addition of 100 μL of phage lysate P1 prepared on the strain BW25113 ΔyncA::Km (about 1.10$^9$ phage/mL)
 Shaking at 37° C. for 3 hours until all cells were lysed
 Addition of 200 μL chloroform and vortexing
 Centrifugation for 10 min at 4500 g to eliminate cell debris
 Transfer of the supernatant to a sterile tube and addition of 200 μL chloroform
 Storage of lysate at 4° C.

Transduction:
 Centrifugation for 10 min at 1500 g of 5 mL over-night culture of the strain MG1655 metA*11 ΔmetJ Ptrc-metH Ptrc36-ARNmst17-metF PtrcF-cysPUWAM PtrcF-cysJIH Ptrc09-gcvTHP ΔpykA ΔpykF ΔpurU in LB medium
 Suspension of the cell pellet in 2.5 mL 10 mM of MgSO$_4$, 5 mM CaCl$_2$
 Control tubes: 100 μL cells
 100 μL phages P1 of strain BW25113 ΔyncA::Km
 Test tubes: 100 μL cells +100 μphages P1 of strain BW25113 ΔyncA::Km
 Incubation for 30 min at 30° C. without shaking
 Addition of 100 μL 1 M sodium citrate to each tube and vortexing
 Addition of 1 mL LB
 Incubation for 1 hour at 37° C. with shaking
 Spreading on LB petri dishes supplemented with kanamycin (50 μg/mL) after centrifuging of tubes for 3 min at 7000 rpm
 Incubation at 37° C. overnight Verification of Strain:
 Kanamycin resistant transformants were selected and the presence of the ΔyncA::Km modification was verified by PCR analysis with the oligonucleotides YncAF and YncAR defined above.

Construction of Strain MG1655 metA*11 ΔmetJ
Ptrc-metH Ptrc36-ARNmst17-metF
PtrcF-cysPUWAM PtrcF-cysJIH ΔpykA ΔpykF
Ptrc09-gcvTHP ΔpurU ΔyncA::Km ΔargA::Cm To inactive the amino-acid acetyltransferase argA gene, the homologous recombination strategy described by Datsenko & Wanner (2000) was used. This strategy allows the insertion of a chloramphenicol resistance cassette, while deleting most of the gene concerned. For this purpose, two oligonucleotides, DargAF and DargAR, were used (reference sequence on the website ecogene.org/):

DargAF (SEQ ID NO 03)
gtggtaaaggaacgtaaaaccgagttggtcgagggattccgccattcggt tccctatatcaataccaccggggaaaaacgTGTAGGCTGGAGCTGCTTC

G with
 a region (lower case) homologous to the argA region from 2947264 to 2947344,
 a region (upper case) for the amplification of the chloramphenicol resistance cassette (reference sequence in Datsenko, K. A. & Wanner, B. L., 2000, PNAS, 97: 6640-6645)

DargAR (SEQ ID NO 04)
ccctaaatccgccatcaacactttggatttacgctggtagttgtacaact gcttttgctctcgggcagtaaatcaatatccCATATGAATATCCTCCTT

AG with
 a region (lower case) homologous to the argA region from 2948592 to 2948511,
 a region (upper case) for the amplification of the chloramphenicol resistance cassette (reference sequence in Datsenko, K. A. & Wanner, B. L., 2000, PNAS, 97: 6640-6645).

The oligonucleotides DargAF and DargAR were used to amplify the chloramphenicol resistance cassette from the plasmid pKD3. The PCR product obtained was introduced by electroporation into the strain MG1655 metA*11 ΔmetJ Ptrc-metH Ptrc36-ARNmst17-metF PtrcF-cysPUWAM PtrcF-cysJIH Ptrc09-gcvTHP ΔpykA ΔpykF ΔpurU ΔyncA::Km (pKD46) in which the expressed Red recombinase enzyme permitted the homologous recombination. Chloramphenicol resistant transformants were selected and the insertion of the resistance cassette was verified by PCR analysis with the oligonucleotides ArgAF and ArgAR defined below (reference sequence on the website ecogene.org/). The strain retained was designated MG1655 metA*11 ΔmetJ Ptrc-metH Ptrc36-ARNmst17-metF PtrcF-cysPUWAM PtrcF-cysJIH Ptrc09-gcvTHP ΔpykA ΔpykF ΔpurU ΔyncA::Km ΔargA::Cm.

ArgAF: cagctgacgatttgattcc (homologous to the argA region from 2946859 to 2946877) (SEQ ID NO 05)
 ArgAR: gggttgtttaatggcgatatcgg (homologous to the argA region from 2949010 to 2948988) (SEQ ID NO 06)

Construction of Strain MG1655 metA*11 ΔmetJ
Ptrc-metH Ptrc36-ARNmst17-metF
PtrcF-cysPUWAM PtrcF-cysJIH ΔpykA ΔpykF
Ptrc09-gcvTHP ΔpurU ΔyncA ΔargA To eliminate the chloramphenicol and kanamycin resistance cassettes, the pCP20 plasmid, carrying recombinase FLP acting on the FRT sites of the chloramphenicol and kanamycin resistance cassettes, is introduced into the recombinant strain MG1655 metA*11 ΔmetJ Ptrc-metH Ptrc36-ARNmst17-metF PtrcF-cysPUWAM PtrcF-cysJIH Ptrc09- gcvTHP ΔpykA ΔpykF ΔpurU ΔyncA::Km ΔargA::Cm by electroporation. After a series of cultures at 42° C., the loss of the chloramphenicol and kanamycin resistance cassettes is verified by PCR analysis with the oligonucleotides described above, YncAF/YncAR and ArgAF/ArgAR. The strain retained is designated MG1655 metA*11 ΔmetJ Ptrc-metH Ptrc36-ARNmst17-metF PtrcF-cysPUWAM PtrcF-cysJIH ΔpykA ΔpykF Ptrc09-gcvTHP ΔpurU ΔyncA ΔargA.

Construction of Strain MG1655 metA*11 ΔmetJ Ptrc-metH Ptrc36-ARNmst17-metF PtrcF-cysPUWAM PtrcF-cysJIH ΔpykA ΔpykF Ptrc09-gcvTHP ΔpurU ΔyncA ΔargA (pME101-thrA*1-cysE-PgapA-metA*11) (pCC1BAC-serB-serA-serC)

The plasmids pME101-thrA*1-cysE-PgapA-metA*11 and pCC1BAC-serB-serA-serC are introduced into strain MG1655 metA*11 ΔmetJ Ptrc-metH Ptrc36-ARNmst17-metF PtrcF-cysPUWAM PtrcF-cysJIH Ptrc09-gcvTHP ΔpykA ΔpykF ΔpurU ΔyncA ΔargA giving rise to MG1655 metA*11 ΔmetJ Ptrc-metH Ptrc36-ARNmst17-metF PtrcF-cysPUWAM PtrcF-cysJIH Ptrc09-gcvTHP ΔpykA ΔpykF ΔpurU ΔyncA ΔargA (pME101-thrA*1-cysE-PgapA-metA*11) (pCC1BAC-serB-serA-serC).

Construction of Synthetic Genes Expressing Amino Acid Acylase Activity

To transform NAM into methionine, NAM acylases (amino acid acylases) were expressed in the methionine producing microorganism.

For this purpose synthetic genes of the pig and *Aspergillus* acyl amino acid acylase genes were prepared by the company Codon Devices. The codon usage and GC content of the genes was adapted to *E. coli* according to the supplier matrix. All sequences with the optimized codon usage are shown below. Expression of the synthetic genes was driven by Ptrc promoters controlled by operator sequences. Transcriptional terminators were added downstream of the genes. The constructs were cloned into pUC19 vectors and verified by sequencing, before transforming them into the methionine producer strains.

*Aspergillus* Acyl Aminoacylase
Promoter and Operator Sequence (SEQ ID NO 07)
Gagctgttgacaattaatcatccggctcgtataatgtgt*ggaattgtgag*
*cggataacaatttcatgacacaggaaacagacc*

*Aspergillus* acyl aminoacylase sequence (XP_001827519.1)
(SEQ ID NO 8)
Mttstvvsllsslmqtqstseheqelahflddhltnlgytverlpiaegs
trenvyaylgtqrktrvcltshldtvppyiplriegstiygrgacddkgp
maaqicaleelraegavkegdvgllfvvgeekggpgmiaanhqdlsfegv
ifgeptegklvvghkghlvfeligegkachsgypqhgvnanfalietlsd
fvqtefpsssllgpstfnvgkieggvsynivpetskalcavrvatdmagi
kkivsdtvarhsnvrlefkfeypetlldhdvegsfnvrsccymnrsilva
hgdneqieideelmegvraykkltmhalnsar (SEQ ID NO 9)
atgaccacgtcgactgtcgtttctctgctgagttcactgatgcagacaca
atccacctcggaacacgagcaggaactggcgcactttctggatgaccatc
tgacaaacctgggatatactgtcgagcgtctgccgattgcagaagggtcc
actcgcgagaacgtctacgcatatctggggacccaactgaaaacgcgtgt
atgtctgacctctcacctggatactgttccgccgtacatcccgctgcgta
ttgagggcagtacaatctatgtcgcgggcttgtgacgataagggcccg
atggctgcacagatctgcgctctggaagagctgcgtgctgaaggtgcggt
caaagaaggcgacgtaggtctgctgttcgtcgttggggaggaaaaagcg
gtccgggcatgatcgcagcgaaccaccaggatctgtcttttgaagggtt -continued atttttggggaaccgacggaaggcaagctggtagtaggtcacaaagggca
cctggttttttgagctgatcggtgagggaaaggcttgtcactccggctacc
cgcaacacggtgtgaacgcgaatttcgccctgattgagacactgtcggat
tttgtccagacggagtttcctagctctagtctgctggggccgtcaacatt
taacgttggcaagatcgaaggtggcgtatcctataatattgtgccggaaa
cgtcgaaagccctgtgtgcagtgcgcgttgcgacggacatggccggtatc
aaaaagattgtgagcgataccgtagcacgtcactctaacgtccgcctgga
gttcaagtttgaatatccagagacactgctggaccatgatgttgaaggga
gttttaatgtgcgttcctgctgttatatgaaccgctccatcctggttgcc
cacggagacaatgagcaaattgaaatcgatgaactgatggagggagtacg
cgcctataaaaagctgacaatgcacgccctgaactcagcccgctaa Transcriptional terminator sequence: (ref: Harrington K. J., Laughlin R. B. and Liang S. Proc Natl Acad Sci USA. 2001 Apr. 24; 98(9):5019-24.)

Tcacactggctcaccttcgggtgggcctttctgc (SEQ ID NO 10)

Pig Acyl Aminoacylase
Promoter and Operator Sequence (SEQ ID NO 11)
Gagctgttgacaattaatcatccggctcgtataatgtgt*ggaattgtgag*
*cggataacaatttcatgacacaggaaacagaac*

Pig acyl aminoacylase sequence (NP_999061.1)
(SEQ ID NO 12)
Maskgregehpsvtlfrqylrirtvqpepdygaavafleerarqlglgcq
kvevvpghvvtvltwpgtnptlssillnshtdvvpvfkehwshdpfegfk
dadgyiygrgaqdmkcvsiqyleavrrlkveghhfprtihmtfvpdeevg
ghqgmelfvkrpefqalragfaldeglasptdaftvfyserspwwlrvts
tgkpghgsrfiedtaaeklhkvinsilafrekekqrlqsnqlkpgavtsv
nltmleggvaynvvpatmsacfdfrvapdvdlkafeeqlqswcqaagegv
tfefvqkwmetqvtsddsdpwwaafsgvfkkmklaleleicpastdaryi
raagvpalgfspmnhtpvllhdhderlheavflrgvdiytqllsalasvp
alpses (SEQ ID NO 13)
atggcgagcaaaggccgtgaaggtgagcatccgtctgtgaccctgtttcg
ccagtatctgcgtattcgcacggttcagcctgaaccggattacggacgag
ctgtggctttcctggaggaacgcgctcgtcagctgggtctgggttgccaa
aaggtagaagttgtcccagggcacgtcgtaactgtactgacttggcctgg
aacgaatccgaccctgagttcaatcctgctgaactcccatacagatgtag
tgccagtgttcaaggaacattggagtcacgacccttttcgaagggtttaaa
gatgccgatggctatatttacggtcgtggggcacaggacatgaagtgtgt
atccattcaatatctggaagctgttcgccgtctgaaagttgaagggcacc
actttccacgcactattcacatgactttcgtgcctgacgaggaagtcggg
ggtcaccaaggtatggaactgttcgtaaaacgccctgagttcaggcact
gcgtgcgggttttgctctggacgagggtctggcgagcccgacagacgcgt
ttaccgtgttttacagtgaacgttcgccttggtggctgcgcgttacttcc
acaggtaagccggggcacggctcgcgtttcatcgaggatacagccgctga
aaagctgcacaaagttattaatagcatcctggcctttcgcgagaaggaaa
agcaacgtctgcagagcaaccagctgaaaccgggtgcggtcactagcgtg
aatctgactatgctggagggggtgtcgcctataacgttgtgccggcaac
tatgagcgcatgcttcgactttcgcgtagctccggatgttgacctgaaag
ccttcgaagaacaactgcagagctggtgtcaagcagcgggagaaggtgta
acctttgagttcgtccagaaatggatggaaacacaggttacctcgactga
tgatagcgatccttggtgggcagccttttctggtgtgttcaaagatatga
agctggcgctggaactggaaatctgcccagcgagtacagacgctcgttac
atccgcgccgcaggcgtaccagccctgggttttttcaccgatgaatcacac
gccggtcctgctgcatgatcacgatgagcgcctgcatgaggcagttttcc
tgcgcggcgtcgacatttatacccaactgctgagtgcactggcttctgtt
cctgcgctgccatcggaatca Transcriptional terminator sequence: (ref: Harrington K. J., Laughlin R. B. and Liang S. Proc Natl Acad Sci USA. 2001 Apr. 24; 98(9):5019-24.)

Tcacactggctcaccttcgggtgggcctttctgc (SEQ ID NO 10)

Example 2

Methionine Production under Fermentation Conditions

Strains that produced substantial amounts of metabolites of interest were tested under production conditions in 2.5 L fermentors (Pierre Guerin) using a fed-batch strategy with phosphate starvation.

To stop growth at a cellular concentration of 30 g·L$^{-1}$, phosphate was added to 28.7 mM to the mineral medium B1b. The fedbatch medium F1 was phosphate free. Briefly, an 8 hour culture grown in 10 mL LB medium with 2.5 g·L$^{-1}$ glucose was used to inoculate a 24 h preculture in minimal medium B1a. These cultures were grown in 500 mL baffled flasks containing 50 mL of minimal medium (B1a) in a rotary shaker (200 RPM) at 37° C.

TABLE 1

Culture batch mineral medium compositions (B1a and B1b).

| Compound | Concentration (g · L$^{-1}$) B1a | Concentration (g · L$^{-1}$) B1b |
|---|---|---|
| Zn(CH$_3$COO)$_2$•2H$_2$O | 0.0130 | 0.0130 |
| CuCl$_2$•2H$_2$O | 0.0015 | 0.0015 |
| MnCl$_2$•4H$_2$O | 0.0150 | 0.0150 |
| CoCl$_2$•6H$_2$O | 0.0025 | 0.0025 |
| H$_3$BO$_3$ | 0.0030 | 0.0030 |
| Na$_2$MoO$_4$•2H$_2$O | 0.0025 | 0.0025 |
| MgSO$_4$•7H$_2$O | 1.00 | 1.00 |
| CaCl$_2$•2H$_2$O | 0.08 | 0.08 |
| Citric acid | 1.70 | 1.70 |
| KH$_2$PO$_4$ | 2.50 | 2.50 |
| K$_2$HPO$_4$•3H$_2$O | 1.38 | 1.38 |
| (NH$_4$)$_2$HPO$_4$ | 0.6040 | 0.6040 |
| Fe(III) citrate H$_2$O | 0.11 | 0.11 |
| (NH$_4$)$_2$S$_2$O$_3$ | 3.70 | 3.70 |
| EDTA | 0.0080 | 0.0080 |
| Thiamine | 0.01 | 0.01 |
| Glucose | 15.00 | 20.00 |
| Vitamin B12 | 0.01 | 0.01 |
| NaOH 8 N | Adjusted to pH 6.8 | Adjusted to pH 6.8 |
| IPTG | 0.0024 | 0.0024 |
| MOPS | 5.00 | 0.00 |

TABLE 2

Culture Fed batch medium composition (F1).

| Compound | Concentration (g · L$^{-1}$) |
|---|---|
| Zn(CH$_3$COO)$_2$,2H$_2$O | 0.0104 |
| CuCl$_2$,2H$_2$O | 0.0012 |
| MnCl$_2$,4H$_2$O | 0.0120 |
| CoCl$_2$•6H$_2$O | 0.0020 |
| H$_3$BO$_3$ | 0.0024 |
| Na$_2$MoO$_4$•2H$_2$O | 0.0020 |
| Fe(III) citrate H$_2$O | 0.0524 |
| MgSO$_4$ | 5.00 |
| (NH$_4$)$_2$S$_2$O$_3$ | 44.10 |
| EDTA | 0.0067 |

TABLE 2-continued

Culture Fed batch medium composition (F1).

| Compound | Concentration (g · L$^{-1}$) |
|---|---|
| Thiamine | 0.01 |
| Glucose | 500.00 |
| Vitamin B12 | 0.01 |
| IPTG | 0.0190 |

Subsequently 2.5L fermentors (Pierre Guerin) were filled with 600 mL of minimal medium (B1b) and were inoculated to a biomass concentration of 0.1 g·L$^{-1}$ with a preculture volume ranging from 25 to 45 mL.

The culture temperature was maintained constant at 37° C. and pH was maintained to the working value (6.8) by automatic addition of NH$_4$OH solutions (NH$_4$OH 10% for 10 hours and 24% until the culture end). The initial agitation rate was set at 200 rpm during the batch phase and was increased to up to 1200 rpm during the fed-batch phase. The initial airflow rate was set at 40 NL·h$^{-1}$ during the batch phase and was increased to 100 NL·h$^{-1}$ at the beginning of the fed-batch phase. Dissolved oxygen concentration was maintained at values between 20 and 40%, preferentially 30% saturation by increasing the agitation.

When the cell mass reached a concentration close to 5 g·L$^{-1}$, the fed-batch was started with an initial flow rate of 5 mL·h$^{-1}$. Feeding solution was injected with a sigmoid profile with an increasing flow rate that reached 21 mL·h$^{-1}$ after 21 hours. The precise feeding conditions were calculated by the equation:

$$Q(t) = p1 + \frac{p2}{1 + e^{-p3(t-p4)}}$$

where Q(t) is the feeding flow rate in mL·h$^{-1}$ for a batch volume of 600 mL with p1=1.15, p2=18.32, p3=0.270, p4=5.

After 21 hours fedbatch, the cellular concentration attained 30 g·L−1, phosphate was depleted from the medium and cells entered in phosphate starvation. At that point, injection of feeding solution was increased to a constant value of 37 mL·h$^{-1}$ for 4 hours. Then, the constant flow rate was decreased to 10 mL·h$^{-1}$ and this flow value was maintained until the end of the fedbatch (50 hours).

Table 3: Maximum methionine/glucose yield ($Y_{met}$), methionine+N-acyl-methionine+N-propionyl-methionine/glucose yield ($Y_{met+NAM}$), N-acetyl-methionine/glucose yield and N-propionyl-methionine/glucose yield (N-acetyl-methionine and N-propionyl-methionine were counted as methionine, % g/g see below) obtained in fed-batch fermentations of strains described above. For the precise definition of yields see below. Mean values of three fermentation runs are shown for the reference strain 1 and of two fedbatch runs for strain 1 DyncA. Strain1 corresponds to MG1655 metA*11 ΔmetJ Ptrc-metH Ptrc36-ARNmst17-metF PtrcF-cysPU-WAM PtrcF-cysJIH ΔpykA ΔpykF Ptrc09-gcvTHP ΔpurU (pME101-thrA*1-cysE-PgapA-metA*11) (pCC1BAC-serB-serA-serC).

| Strain | $Y_{met}$ (% g · g⁻¹) | $Y_{met+NAM}$ (% g · g⁻¹) | $Y_{N\text{-}acetyl\text{-}methionine}$ (% g · g⁻¹) | $Y_{N\text{-}propionyl\,methionine}$ (% g · g⁻¹) |
|---|---|---|---|---|
| Reference strain (Strain 1) | 16.97 ± 1.00 | 20.03 ± 0.83 | 2.65 ± 0.17 | 0.41 ± 0.13 |
| Strain 1 DyncA | 18.33 ± 1.37 | 18.62 ± 1.24 | 0.27 ± 0.15 | 0.02 ± 0.01 |

Determination of Methionine/Glucose Yield ($Y_{met}$)

Extracellular methionine concentration was quantified by HPLC after OPA/FMOC derivatization. The N-acetyl-methionine and residual glucose concentrations were analyzed using HPLC with refractometric detection. The N-propionyl methionine concentration was determinated by GC-MS after silylation, it was expressed as N-acetyl-methionine equivalent.

The fermentor volume was calculated by adding to the initial volume the amount of solutions added to regulate the pH and to feed the culture and by subtracting the volume used for sampling and lost by evaporation.

The fedbatch volume was followed continuously by weighing the feeding stock. The amount of injected glucose was then calculated on the basis of the injected weight, the density of the solution and the glucose concentration controlled by the method of Brix ([Glucose]). The methionine yield was expressed as followed:

$$Y_{met} = \frac{Methionine_t * V_t - Methionine_0 * V_0}{Consummed\ glucose_t} * 100$$

With Methionine₀ and Methionine$_t$ respectively the initial and methionine concentrations at time (t) and V₀ and V$_t$ the initial and the instant t volumes.

The $Y_{N\text{-}acetyl\text{-}methionine}$ was calculated as followed:

$$Y_{N\text{-}acetyl\ methionine} = \frac{N\text{-}acetyl\ methionine_t * V_t}{Consummed\ glucose_t} * 100 * 0.1492,$$

with N-acetyl-methionine$_t$, the concentration in mmol per liter at the instant t.

The $Y_{N\text{-}propionyl\ methionine}$ was calculated as followed:

$$Y_{N\text{-}propionyl\ methionine} = \frac{N\text{-}propionyl\ methionine_t * V_t}{Consummed\ glucose_t} * 100 * 0.1492$$

with N-propionyl methionine$_t$, the concentration in mmol per liter at the instant t.

The $Y_{Met+N\text{-}acetyl\text{-}methionine+N\text{-}propionyl\text{-}methionine}$ ($Y_{Met+NAM}$) was calculated as follows:

$$Y_{Met+NAM} = \frac{Methionine_t * V_t + N\text{-}acetyl\text{-}methionine_t * V_t * 0{,}1492 + N\text{-}propionyl\text{-}methionine * V_t * 0{,}1492}{Consummed\ glucose_t} * 100$$

With Methionine$_t$ the methionine concentration in g per liter, N-acetyl-methionine$_t$ and N-propionyl-methionine$_t$, the respective concentrations in mmol per liter at the instant t.

The consumed glucose was calculated as follows:

$$fed\ volume_t = \frac{fed\ weight_0 - fed\ weight_t}{density\ fed\ solution}$$

Injected $Glucose_t$ = $fed\ volume_t$ * [Glucose]

Consumed $glucose_t$ =

[Glucose]₀ * V₀ + Injected Glucose − [Glucose]$_{residual}$ * V$_t$

With [Glucose]₀, [Glucose], [Glucose]$_{residual}$ respectively the initial, the fed and the residual glucose concentrations.

Example 3

Adapting Culture Conditions by Adding Amino Acid Acylase to the Fermentation Medium To transform N-acetyl-methionine into methionine and acetate 160 U of N-amino acid acylase (porcine kidney, Sigma) were added to 200 µl fermentation broth after the fermentation run of strain 1 (performed as described above). The reaction mixture was incubated at 37° C. for 2 h. Subsequently methionine and N-acetyl-methionine concentrations were determined as described above. 75-95% of N-acetyl-methionine was transformed into methionine by this enzymatic treatment.

Non-Patent References

Figge R M (2006), ed Wendisch V F, Microbiol Monogr (5) Amino acid biosynthesis p164-185,
Polevoda & Sherman 2000 JBC 275, 47, pp 36479-36482,
Driessen et al. 1985, CRC Crit. Rev. Biochem. 18, 281-325,
Marvil & Leisinger 1977 JBC 252, 10 pp. 3295-3303,
Javid-Majd & Blanchard 2000 Biochemistry 39, 1285-93,
Giardina et al 2000 Eur. J. Biochem. 267, 6249-55,
Gentzen et al. 1980 Z. Naturforsch 35 c, 544-50,
Manting & Driessen 2000 Mol Microbiol 37, 226-38,
Choi & Lee 2004 Appl. Microbiol. Biotechnol. 64, 625-635,
Jacob-Dubuisson et al. 2004 Biochim et Biophys Act 1694 235-257,
José & Meyer 2007 Microbiol and Molecul Biol Rev 71, 600-19,
Shokri et al 2003 Appl Microbiol Biotechnol 60, 654-64,
Anderson, 1946, *Proc. Natl. Acad. Sci. USA* 32:120-128,
Miller, 1992; A Short Course in Bacterial Genetics: A Laboratory Manual and Handbook for *Escherichia coli* and Related Bacteria, Cold Spring Harbor Laboratory Press, Cold Spring Harbor, N.Y.,
Schaefer et al. (1999, *Anal. Biochem.* 270: 88-96),
Liebl et al., 1989, *Appl. Microbiol. Biotechnol.* 32: 205-210,
Riedel et al. (2001, *J. Mol. Microbiol. Biotechnol.* 3: 573-583), Datsenko, K. A. & Wanner, B. L. (2000) "One-step inactivation of chromosomal genes in *Escherichia coli* K-12 using PCR products". Proc. Natl. Acad. Sci. USA 97: 6640-6645, Carrier and Keasling (1998) Biotechnol. Prog. 15, 58-64, Sambrook et al. (1989 Molecular Cloning: a Laboratory Manual. 2$^{nd}$ ed. Cold Spring Harbor Lab., Cold Spring Harbor, N.Y.).

The invention claimed is:

1. A method for the production of methionine and/or its derivatives, in a fermentative process comprising the following steps:
culturing a modified *E. coli* cell in an appropriate culture medium comprising a source of carbon, a source of sulphur and a source of nitrogen; and
recovering methionine and/or its derivatives from the culture medium,
wherein the accumulation of N-acyl methionine in the culture medium is reduced compared to a corresponding *E. coli* cell that produces methionine, wherein the corresponding *E. coli* cell comprises a deletion in the endogenous metJ gene and overexpresses a gene encoding a serine acetyltransferase (cysA) and a gene encoding a methionine synthase (metH), by increasing the number of copies of the genes and/or using a stronger promoter, and wherein the modified *E. coli* cell comprises a deletion in the endogenous metJ gene, overexpresses said gene encoding the serine acetyltransferase and said gene encoding the methionine synthase by increasing the number of copies of the genes and/or using a stronger promoter, and comprises a disruption in an endogenous yncA, argA, yjdJ, yfaP, yedL, and/or yjhQ gene.

2. The method of claim 1, wherein the modified *E. coli* cell comprises a disruption in the endogenous yncA gene.

3. The method of claim 1, wherein the modified *E. coli* cell comprises a disruption in the endogenous argA gene.

4. The method of claim 1, wherein the modified *E. coli* cell comprises a disruption in the endogenous yjdJ, yfaP, yedL, and yjhQ genes.

5. The method of claim 2, wherein the modified *E. coli* cell comprises a disruption in the endogenous argA gene.

6. The method of claim 1, wherein the N-acyl methionine whose accumulation is reduced is N-acetyl-methionine and/or N-propionyl-methionine.

7. The method of claim 1, wherein the modified *E. coli* cell further overexpresses a homoserine succinyltransferase allele encoding a homoserine succinyltransferase with reduced feedback sensitivity to its inhibitors S-adenosyl-methionine (SAM) and methionine by increasing the number of copies of the allele and/or using a stronger promoter.

8. The method of claim 1, wherein the modified *E. coli* cell further overexpresses a gene encoding a methylenetetrahydrofolate reductase (metF) by increasing the number of copies of the gene and/or using a stronger promoter.

9. The method of claim 1, wherein the source of sulphur in the culture medium is sulfate, thiosulfate, hydrogen sulfide, dithionate, dithionite, sulfite, methylmercaptan, dimethyldisulfide or a combination thereof.

10. The method of claim 1, wherein the source of sulphur in the culture medium is sulfate, thiosulfate, or a mixture thereof.

11. The method of claim 1, wherein the source of carbon is derived from renewable feed-stock.

12. The method of claim 1, wherein the source of carbon is glucose or sucrose.

13. The method of claim 1, wherein the source of nitrogen is supplied in the form of ammonium ($NH_4^+$) or ammonia ($NH_3$).

14. The method of claim 1, wherein the recovering comprises isolating methionine.

15. The method of claim 1, wherein the modified *E. coli* cell is limited or starved for phosphate and/or potassium.

16. The method of claim 1, wherein the production of N-acyl-methionine is reduced by expressing at least one native or heterologous N-acyl-L-amino-acid amidohydrolase enzyme in the modified *E. coli* cell, wherein said N-acyl-L-amino-acid amidohydrolase enzyme is selected from the group consisting of an *Aspergillus* N-acylamino acid acylase, a pig N-acylamino acid acylase, and an acetylornithine deacetylase (argE).

17. The method of claim 1, wherein the production of N-acyl-methionine is reduced by adapting the culture conditions selected among pH, oxygenation and/or temperature, or by adding a N-acyl amino acid acylase into the medium.

\* \* \* \* \*

```
                         SEQUENCE LISTING

<160> NUMBER OF SEQ ID NOS: 13

<210> SEQ ID NO 1
<211> LENGTH: 21
<212> TYPE: DNA
<213> ORGANISM: Artificial
<220> FEATURE:
<223> OTHER INFORMATION: Oligonucleotide

<400> SEQUENCE: 1
gtttgccgat tgccccacc g                                            21

<210> SEQ ID NO 2
<211> LENGTH: 20
<212> TYPE: DNA
<213> ORGANISM: Artificial
<220> FEATURE:
<223> OTHER INFORMATION: Oligonucleotide

<400> SEQUENCE: 2
cgcccatcac ggtcgcaagc                                             20

<210> SEQ ID NO 3
<211> LENGTH: 101
<212> TYPE: DNA
<213> ORGANISM: Artificial
<220> FEATURE:
<223> OTHER INFORMATION: Oligonucleotide

<400> SEQUENCE: 3
gtggtaaagg aacgtaaaac cgagttggtc gagggattcc gccattcggt tccctatatc    60
aatacccacc ggggaaaaac gtgtaggctg gagctgcttc g                       101

<210> SEQ ID NO 4
<211> LENGTH: 102
<212> TYPE: DNA
<213> ORGANISM: Artificial
<220> FEATURE:
<223> OTHER INFORMATION: Oligonucleotide

<400> SEQUENCE: 4
ccctaaatcc gccatcaaca ctttggattt acgctggtag ttgtacaact gcttttttgct   60 ctcgggcagt aaatcaatat cccatatgaa tatcctcctt ag                     102

<210> SEQ ID NO 5
<211> LENGTH: 19
<212> TYPE: DNA
<213> ORGANISM: Artificial
<220> FEATURE:
<223> OTHER INFORMATION: Oligonucleotide

<400> SEQUENCE: 5
cagctgacga tttgattcc                                               19

<210> SEQ ID NO 6
<211> LENGTH: 23
<212> TYPE: DNA
<213> ORGANISM: Artificial
<220> FEATURE:
```

<223> OTHER INFORMATION: Oligonucleotide

<400> SEQUENCE: 6
gggttgttta atggcgatat cgg    23

<210> SEQ ID NO 7
<211> LENGTH: 83
<212> TYPE: DNA
<213> ORGANISM: Aspergillus niger

<400> SEQUENCE: 7
gagctgttga caattaatca tccggctcgt ataatgtgtg gaattgtgag cggataacaa    60
tttcatgaca caggaaacag acc    83

<210> SEQ ID NO 8
<211> LENGTH: 331
<212> TYPE: PRT
<213> ORGANISM: Aspergillus niger

<400> SEQUENCE: 8

```
Met Thr Thr Ser Thr Val Val Ser Leu Leu Ser Ser Leu Met Gln Thr
1               5                   10                  15

Gln Ser Thr Ser Glu His Glu Gln Glu Leu Ala His Phe Leu Asp Asp
            20                  25                  30

His Leu Thr Asn Leu Gly Tyr Thr Val Glu Arg Leu Pro Ile Ala Glu
        35                  40                  45

Gly Ser Thr Arg Glu Asn Val Tyr Ala Tyr Leu Gly Thr Gln Arg Lys
    50                  55                  60

Thr Arg Val Cys Leu Thr Ser His Leu Asp Thr Val Pro Pro Tyr Ile
65                  70                  75                  80

Pro Leu Arg Ile Glu Gly Ser Thr Ile Tyr Gly Arg Gly Ala Cys Asp
                85                  90                  95

Asp Lys Gly Pro Met Ala Ala Gln Ile Cys Ala Leu Glu Glu Leu Arg
            100                 105                 110

Ala Glu Gly Ala Val Lys Glu Gly Asp Val Gly Leu Leu Phe Val Val
        115                 120                 125

Gly Glu Glu Lys Gly Gly Pro Gly Met Ile Ala Ala Asn His Gln Asp
    130                 135                 140

Leu Ser Phe Glu Gly Val Ile Phe Gly Glu Pro Thr Glu Gly Lys Leu
145                 150                 155                 160

Val Val Gly His Lys Gly His Leu Val Phe Glu Leu Ile Gly Glu Gly
                165                 170                 175

Lys Ala Cys His Ser Gly Tyr Pro Gln His Gly Val Asn Ala Asn Phe
            180                 185                 190

Ala Leu Ile Glu Thr Leu Ser Asp Phe Val Gln Thr Glu Phe Pro Ser
        195                 200                 205

Ser Ser Leu Leu Gly Pro Ser Thr Phe Asn Val Gly Lys Ile Glu Gly
    210                 215                 220

Gly Val Ser Tyr Asn Ile Val Pro Glu Thr Ser Lys Ala Leu Cys Ala
225                 230                 235                 240

Val Arg Val Ala Thr Asp Met Ala Gly Ile Lys Lys Ile Val Ser Asp
                245                 250                 255

Thr Val Ala Arg His Ser Asn Val Arg Leu Glu Phe Lys Phe Glu Tyr
            260                 265                 270

Pro Glu Thr Leu Leu Asp His Asp Val Glu Gly Ser Phe Asn Val Arg
        275                 280                 285
```

```
Ser Cys Cys Tyr Met Asn Arg Ser Ile Leu Val Ala His Gly Asp Asn
        290                 295                 300

Glu Gln Ile Glu Ile Asp Glu Leu Met Glu Gly Val Arg Ala Tyr Lys
305                 310                 315                 320

Lys Leu Thr Met His Ala Leu Asn Ser Ala Arg
                325                 330

<210> SEQ ID NO 9
<211> LENGTH: 996
<212> TYPE: DNA
<213> ORGANISM: Aspergillus niger

<400> SEQUENCE: 9
atgaccacgt cgactgtcgt ttctctgctg agttcactga tgcagacaca atccacctcg      60
gaacacgagc aggaactggc gcactttctg gatgaccatc tgacaaacct gggatatact     120
gtcgagcgtc tgccgattgc agaagggtcc actcgcgaga cgtctacgc atatctgggg      180 acccaacgta aaacgcgtgt atgtctgacc tctcacctgg atactgttcc gccgtacatc     240
ccgctgcgta ttgagggcag tacaatctat ggtcgcgggg cttgtgacga taagggcccg     300
atggctgcac agatctgcgc tctggaagag ctgcgtgctg aaggtgcggt caaagaaggc     360
gacgtaggtc tgctgttcgt cgttggggag gaaaaaggcg gtccgggcat gatcgcagcg     420
aaccaccagg atctgtcttt tgaagggggtt attttttgggg aaccgacgga aggcaagctg   480
gtagtaggtc acaaagggca cctggttttt gagctgatcg gtgagggaaa ggcttgtcac    540
tccggctacc cgcaacacgg tgtgaacgcg aatttcgccc tgattgagac actgtcggat    600
tttgtccaga cggagtttcc tagctctagt ctgctggggc cgtcaacatt taacgttggc    660
aagatcgaag gtggcgtatc ctataatatt gtgccggaaa cgtcgaaagc cctgtgtgca    720
gtgcgcgttg cgacggacat ggccggtatc aaaaagattg tgagcgatac cgtagcacgt    780
cactctaacg tccgcctgga gttcaagttt gaatatccag agacactgct ggaccatgat    840
gttgaaggga gttttaatgt gcgttcctgc tgttatatga accgctccat cctggttgcc    900
cacggagaca tgagcaaat tgaaatcgat gaactgatgg agggagtacg cgcctataaa    960
aagctgacaa tgcacgccct gaactcagcc cgctaa                              996

<210> SEQ ID NO 10
<211> LENGTH: 34
<212> TYPE: DNA
<213> ORGANISM: Artificial
<220> FEATURE:
<223> OTHER INFORMATION: Transcriptional terminator sequence

<400> SEQUENCE: 10
tcacactggc tcaccttcgg gtgggccttt ctgc                                 34

<210> SEQ ID NO 11
<211> LENGTH: 83
<212> TYPE: DNA
<213> ORGANISM: Sus scrofa

<400> SEQUENCE: 11
gagctgttga caattaatca tccggctcgt ataatgtgtg gaattgtgag cggataacaa     60
tttcatgaca caggaaacag aac                                             83

<210> SEQ ID NO 12
<211> LENGTH: 407
<212> TYPE: PRT
<213> ORGANISM: Sus scrofa
```

<400> SEQUENCE: 12

```
Met Ala Ser Lys Gly Arg Glu Gly Glu His Pro Ser Val Thr Leu Phe
1               5                   10                  15

Arg Gln Tyr Leu Arg Ile Arg Thr Val Gln Pro Glu Pro Asp Tyr Gly
            20                  25                  30

Ala Ala Val Ala Phe Leu Glu Glu Arg Ala Arg Gln Leu Gly Leu Gly
        35                  40                  45

Cys Gln Lys Val Glu Val Val Pro Gly His Val Val Thr Val Leu Thr
    50                  55                  60

Trp Pro Gly Thr Asn Pro Thr Leu Ser Ser Ile Leu Leu Asn Ser His
65                  70                  75                  80

Thr Asp Val Val Pro Val Phe Lys Glu His Trp Ser His Asp Pro Phe
                85                  90                  95

Glu Gly Phe Lys Asp Ala Asp Gly Tyr Ile Tyr Gly Arg Gly Ala Gln
            100                 105                 110

Asp Met Lys Cys Val Ser Ile Gln Tyr Leu Glu Ala Val Arg Arg Leu
        115                 120                 125

Lys Val Glu Gly His His Phe Pro Arg Thr Ile His Met Thr Phe Val
130                 135                 140

Pro Asp Glu Glu Val Gly Gly His Gln Gly Met Glu Leu Phe Val Lys
145                 150                 155                 160

Arg Pro Glu Phe Gln Ala Leu Arg Ala Gly Phe Ala Leu Asp Glu Gly
                165                 170                 175

Leu Ala Ser Pro Thr Asp Ala Phe Thr Val Phe Tyr Ser Glu Arg Ser
            180                 185                 190

Pro Trp Trp Leu Arg Val Thr Ser Thr Gly Lys Pro Gly His Gly Ser
        195                 200                 205

Arg Phe Ile Glu Asp Thr Ala Ala Glu Lys Leu His Lys Val Ile Asn
    210                 215                 220

Ser Ile Leu Ala Phe Arg Glu Lys Glu Lys Gln Arg Leu Gln Ser Asn
225                 230                 235                 240

Gln Leu Lys Pro Gly Ala Val Thr Ser Val Asn Leu Thr Met Leu Glu
                245                 250                 255

Gly Gly Val Ala Tyr Asn Val Val Pro Ala Thr Met Ser Ala Cys Phe
            260                 265                 270

Asp Phe Arg Val Ala Pro Asp Val Asp Leu Lys Ala Phe Glu Glu Gln
        275                 280                 285

Leu Gln Ser Trp Cys Gln Ala Gly Glu Gly Val Thr Phe Glu Phe
    290                 295                 300

Val Gln Lys Trp Met Glu Thr Gln Val Thr Ser Thr Asp Asp Ser Asp
305                 310                 315                 320

Pro Trp Trp Ala Ala Phe Ser Gly Val Phe Lys Asp Met Lys Leu Ala
                325                 330                 335

Leu Glu Leu Glu Ile Cys Pro Ala Ser Thr Asp Ala Arg Tyr Ile Arg
            340                 345                 350

Ala Ala Gly Val Pro Ala Leu Gly Phe Ser Pro Met Asn His Thr Pro
        355                 360                 365

Val Leu Leu His Asp His Asp Glu Arg Leu His Glu Ala Val Phe Leu
    370                 375                 380

Arg Gly Val Asp Ile Tyr Thr Gln Leu Leu Ser Ala Leu Ala Ser Val
385                 390                 395                 400

Pro Ala Leu Pro Ser Glu Ser
                405
```

```
<210> SEQ ID NO 13
<211> LENGTH: 1221
<212> TYPE: DNA
<213> ORGANISM: Sus scrofa

<400> SEQUENCE: 13
atggcgagca aaggccgtga aggtgagcat ccgtctgtga ccctgtttcg ccagtatctg      60
cgtattcgca cggttcagcc tgaaccggat tacggagcag ctgtggcttt cctggaggaa     120
cgcgctcgtc agctgggtct gggttgccaa aaggtagaag ttgtcccagg gcacgtcgta     180
actgtactga cttggcctgg aacgaatccg accctgagtt caatcctgct gaactcccat     240
acagatgtag tgccagtgtt caaggaacat tggagtcacg acccttcga agggtttaaa     300
gatgccgatg gctatattta cggtcgtggg gcacaggaca tgaagtgtgt atccattcaa     360
tatctggaag ctgttcgccg tctgaaagtt gaagggcacc actttccacg cactattcac     420
atgactttcg tgcctgacga ggaagtcggg ggtcaccaag gtatggaact gttcgtaaaa     480
cgccctgagt ttcaggcact gcgtgcgggt tttgctctgg acgagggtct ggcgagcccg     540
acagacgcgt ttaccgtgtt ttacagtgaa cgttcgcctt ggtggctgcg cgttacttcc     600
acaggtaagc cggggcacgg ctcgcgtttc atcgaggata cagccgctga aaagctgcac     660
aaagttatta atagcatcct ggcctttcgc gagaaggaaa agcaacgtct gcagagcaac     720
cagctgaaac cgggtgcggt cactagcgtg aatctgacta tgctggaggg gggtgtcgcc     780
tataacgttg tgccggcaac tatgagcgca tgcttcgact ttcgcgtagc tccggatgtt     840
gacctgaaag ccttcgaaga caactgcag agctggtgtc aagcagcggg agaaggtgta     900
acctttgagt tcgtccagaa atggatgaa acacaggtta cctcgactga tgatagcgat     960
ccttggtggg cagccttttc tggtgtgttc aaagatatga agctggcgct ggaactggaa    1020
atctgcccag cgagtacaga cgctcgttac atccgcgccg caggcgtacc agccctgggt    1080
ttttcaccga tgaatcacac gccggtcctg ctgcatgatc acgatgagcg cctgcatgag    1140
gcagttttcc tgcgcggcgt cgacatttat acccaactgc tgagtgcact ggcttctgtt    1200
cctgcgctgc catcggaatc a                                             1221
```